(12) United States Patent
Lauria et al.

(10) Patent No.: US 6,673,805 B2
(45) Date of Patent: *Jan. 6, 2004

(54) PLATINUM DERIVATIVE PHARMACEUTICAL FORMULATIONS

(75) Inventors: Sara Lauria, Monzo (IT); Alessandro Martini, Milan (IT); Cristina Ciocca, Motta Visconti (IT)

(73) Assignee: Pharmacia Italia S.p.A., Milan (IT)

( * ) Notice: Subject to any disclaimer, the term of this patent is extended or adjusted under 35 U.S.C. 154(b) by 54 days.

This patent is subject to a terminal disclaimer.

(21) Appl. No.: 10/225,607

(22) Filed: Aug. 22, 2002

(65) Prior Publication Data

US 2003/0109514 A1 Jun. 12, 2003

Related U.S. Application Data

(63) Continuation-in-part of application No. 10/010,122, filed on Dec. 6, 2001, now Pat. No. 6,476,068.

(51) Int. Cl.⁷ ............................................. A61K 31/44
(52) U.S. Cl. ...................................... 514/283; 514/492
(58) Field of Search ................................ 514/492, 283

(56) References Cited

U.S. PATENT DOCUMENTS

| | | | |
|---|---|---|---|
| 4,169,846 A | 10/1979 | Kidani et al. | 260/429 |
| 5,290,961 | 3/1994 | Okamoto et al. | 556/137 |
| 5,298,642 | 3/1994 | Tozawa et al. | 556/137 |
| 5,338,874 | 8/1994 | Nakanishi et al. | 556/137 |
| 5,420,319 | 5/1995 | Okamoto et al. | 556/137 |
| 5,633,016 | 5/1997 | Johnson | 424/649 |
| 5,716,988 | 2/1998 | Ibrahim et al. | 514/492 |
| 5,945,122 | 8/1999 | Abra et al. | 424/450 |
| 5,959,133 | 9/1999 | Ohnishi | 556/137 |
| 6,056,973 | 5/2000 | Allen et al. | 424/450 |
| 6,063,780 | 5/2000 | Dexter et al. | 514/243 |
| 6,066,666 | 5/2000 | Covey et al. | 514/424 |
| 6,066,668 | 5/2000 | Hausheer et al. | 514/492 |
| 6,287,593 | 9/2001 | Cherian | 424/450 |
| 6,306,903 | 10/2001 | Pevarello et al. | 514/492 |

FOREIGN PATENT DOCUMENTS

| | | |
|---|---|---|
| EP | 0715854 A2 | 6/1996 |
| EP | 0715854 A3 | 6/1996 |
| EP | 1121117 A2 | 8/2001 |
| WO | 9412193 | 6/1997 |
| WO | 0021527 | 4/2000 |
| WO | 0115691 A1 | 3/2001 |
| WO | 0166102 A2 | 9/2001 |

OTHER PUBLICATIONS

Bissery, United States Patent Application Publication, Pub. No. US 2001/0041712 A1, Nov. 15, 2001.

Khokhar, et al., "Toxicity and efficacy studies on a series of lipid–soluable dineodecanoato (trans–R,R–and trans–S, S–1,2–diaminocyclohexane) platinum (II) complexes entrapped in liposomes", Anti–Cancer Drugs, vol. 3, pp. 95–100 (1992).

Bleiberg, "CPT–11 in Gastrointestinal Cancer", European Journal of Cancer, vol. 35, No. 3, pp. 371–379 (1999).

Wasserman, et al., "Oxaliplatin (L–OHP) and Irinotecan (CPT11) Phase I/II Studies: Results in 5 FU Refractory (FR) Colorectal Cancer (CRC) Patients (pts)", Proc. Am. Soc. Clin. Oncol., 18, 35 Meet., 238a (1999).

Wasserman, et al., "Combination of Oxaliplatin Plus Irinotecan in Patients with Gastrointestinal Tumors: Results of Two Independent Phase I Studies with Pharmacokinetics", Journal of Clinical Oncology, vol. 16, No. 7, pp. 1751–1759 (1999).

Veal, et al., "A Phase I Study of Paediatric Patients to Evaluate the Safety and Pharmacokinetics of SPI–77, a Liposome Encapsulated Formulation of Cisplatin", British Journal Of Cancer, vol. 84 (8), pp. 1029–1035 (2001).

Curis, et al., "Carboplatin and Oxaliplatin Decomposition in Chloride Medium, Monitored by XAS", J. Synchrotron Rad., vol. 8, pp. 716–718 (2001).

Primary Examiner—James H Reamer
(74) Attorney, Agent, or Firm—McDonnell Boehnen Hulbert & Berghoff

(57) ABSTRACT

The present invention relates to novel stable solution formulations comprising oxaliplatin alone or in combination with irinotecan (CPT-11), an effective stabilizing amount of lactic acid and/or a pharmaceutically acceptable salt thereof and a pharmaceutically acceptable carrier. A method for manufacturing such formulations ready for administration and their use in the antitumor therapy are also within the scope of the invention.

14 Claims, No Drawings

PLATINUM DERIVATIVE PHARMACEUTICAL FORMULATIONS

PRIORITY

This application is a continuation-in-part application of U.S. application Ser. No. 10/010,122 filed Dec. 6, 2001 now U.S. Pat. No. 6,476,068, which is incorporated by reference herein in its entirety.

FIELD OF THE INVENTION

The present invention pertains to the field of pharmaceutical compositions for the treatment of neoplastic diseases and, particularly, it relates to pharmaceutical formulations comprising a platinum derivative.

SUMMARY OF THE INVENTION

The present invention is directed to novel stable formulations of oxaliplatin alone or combined in fixed ratios with irinotecan, wherein lactic acid and/or a pharmaceutically acceptable salt thereof serves as a novel mean for preparing a dosage unit with an improved stability. A method for manufacturing such formulations ready for administration and their use in the antitumor therapy are also within the scope of the invention.

BACKGROUND OF THE INVENTION

Oxaliplatin, also known as L-OHP, is a third generation platinum complex.

The term "oxaliplatin" as used herein, includes cis-oxalato(trans-l-1,2-diaminocyclohexane)platinum(II), its optic enatiomer cis-oxalato(trans-d-1,2-diaminocyclohexane)platinum(II) and any racemic mixture thereof. The term "oxaliplatin" also includes cis-oxalato (trans-l-1,2-diaminocyclohexane) platinum (II) having high optical purity, namely an optical purity equal to or higher than about 99.5%, for example a cis-oxalato (trans-l-1,2-diaminocyclohexane) platinum(II), wherein the melting point is between about 198° C. and about 292° C., obtained following the procedure described in Tanaka U.S. Pat. No. 5,338,874 and, especially, a cis-oxalato(trans-l-1,2-cyclohexanediamine)platinum(II), which possesses optical purity of about 99.94% or more and a melting point between about 198.3° C. and about 199.7° C., obtained following the procedure disclosed in Tanaka U.S. Pat. No. 5,420,319.

Oxaliplatin has entered clinical development and achieved approval for marketing. During its development, oxaliplatin has aroused lively interest due, firstly, to its in vitro and in vivo antitumoral activity, especially in cisplatin-resistant models and cell lines expressing resistance genes, and, secondly, to its good clinical tolerance, the absence of renal or auditory toxicity being combined with a low hematotoxicity. Combined with other antitumoral agent cytotoxic agents (5-FU, raltitrexed, irinotecan or cisplatin), oxaliplatin produces an additive and often synergistic cytotoxic effect. The oxaliplatin-5FU+FA combination is now well established in metastatic colorectal cancer. Regarding its particular cytotoxic characteristics and its activity in mismatch repair deficient cells (which are resistant to cisplatin and carboplatin), oxaliplatin is shown potential in a large variety of solid tumor types, notably in association with other cytotoxic agents, thus opening the path to a wider range of indications. Kidani et al,. U.S. Pat. No. 4,169,846, discloses cis-platinum(II) complexes of 1,2-diaminocyclohexane active as antitumor compounds. Cis-oxalato(trans-l-1,2-diaminocyclohexane)platinum(II) is specifically disclosed in Example 4(i).

SmithKline Beecham, U.S. Pat. No. 5,633,016, discloses a method for inhibiting tumour cell growth using synergistic combination of a camptothecin analogue and a platinum coordination compound, e.g. cisplatin and oxaliplatin.

Tanaka, U.S. Pat. No. 5,290,961, discloses a process for preparing various platinum compounds including oxaliplatin, which comprises adding silver ion solution to cis-platinum (II) di halogen compound, filtering of silver halide, adding iodide compound and active carbon then adding organic di basic acid.

Tanaka, U.S. Pat. Nos. 5,338,874, 5,298,642 and 5,420,319, disclose optically pure oxaliplatin and methods for preparing the same.

Debiopharm, International patent application WO94/12193, discloses a freeze-dried composition for jointly administering cisplatin and oxaliplatin.

Tanaka, U.S. Pat. No. 5,420,319, discloses oxaliplatin having high optical purity and a process for obtaining it.

Debiopharm, U.S. Pat. No. 5,716,988, discloses a stable oxaliplatin preparation for parenteral administration comprising an aqueous solution of oxaliplatin, in a concentration of 1 to 5 mg/ml, and with a pH in the range of 4.5 to 6.

Tanaka, European patent application No. 715,854, discloses a combination of: (a) at least one of cisplatin, carboplatin, 5-fluorouracil (5-FU), tegaful, carmoful, doxifluridine, uracil, irinotecan, adriamycin, etoposide, mitomycin, mitoxantrone and bleomycin; and (b) oxaliplatin, which produces an additive or synergistic effect on killing cells during cancer therapy.

Tanaka, U.S. Pat. No. 5,959,133, discloses high-yielding process for obtaining chelating platinum complexes including oxaliplatin, which does not contain dihydroxoplatinum complex impurity.

Pharmacia & Upjohn Co., U.S. Pat. No. 6,287,593, discloses a phospholipid complex of a platinum dicarboxylate including oxaliplatin, which can be reconstituted in a pharmaceutically acceptable vehicle with or without lyophilization and administered to a patient in the treatment of cancer and other diseases.

Debiopharm, European patent application No. 1121117 discloses a liquid pharmaceutical preparation of oxaliplatin packaged in a container, preferably in a sealed soft bag for medical use. The liquid preparation of oxaliplatin can advantageously be presented in the form of a bag with several compartments containing doses of a ready-to-use solution.

Sanofi-Synthelabo, U.S. Pat. No. 6,063,780, discloses a treatment of mammalian solid tumors with the co-administration of 3-amino-1,2,4-benzotriazine 1,4-dioxide (tirapazamine) paclitaxel and oxaliplatin.

Debiopharm, International patent application No. WO 01/15691, discloses stable solutions of oxaliplatin, ready for parenteral administration, containing 1,2-propane diol, glycerol, maltitol, sucrose,and/or inositol.

BioNumerik, U.S. Pat. No. 6,066,666, discloses pharmaceutical formulations comprising a platinum analogue compound, e.g. oxaliplatin and a protective agent having either a sulfhydryl moiety or being reducible disulfide.

Bristol-Myers Squibb, International patent application WO 01/66102 discloses oral dosage forms for administration of the combination of tegafur+uracil (UFT), folinic acid, and oxaliplatin and methods of using the same.

Sanofi-Synthelabo, U.S. Pat. No. 6,306,902, discloses a stable oxaliplatin solution formulation comprising a therapeutically effective amount of oxaliplatin, an effective stabilizing amount of a buffering agent and a pharmaceutically acceptable carrier wherein the buffering agent is oxalic acid or an alkali metal salt thereof.

Bissery M. C., U.S. patent application Ser. No. 20010041712 discloses anticancer treatments with associations of camptothecin derivatives such as irinotecan (CPT-11, CAMPTOSAR®), topotecan, 9-aminocamptothecin, 9-nitrocamptothecin, and platinum derivatives including cis-platin (cis-platinum, cis-diaminedichloroplatinum, or CDDP), carboplatin, and oxaliplatin.

At present, oxaliplatin is solely marketed in the form of lyophilized preparations, which need to be reconstituted before administration. The currently marketed formulation is a lyophilized powder (50, 100 mg) to be reconstituted just before administration to a patient with water for injection or a 5% glucose solution and finally diluted with a 5% glucose solution (0.2 mg/ml final concentration).

The lyophilized oxaliplatin can present some disadvantages, which do not render particularly attractive the use of this product in such a pharmaceutical form.

Both the manufacturing and the reconstitution of such preparations expose the involved personnel (workers, pharmacists, medical personnel, nurses) to risks of contamination, which are particularly serious due to the toxicity of the antitumor substances. To administer a lyophilized preparation, double handling of the drug is required, the lyophilized cake having to be first reconstituted and then administered and, moreover, in some cases, the complete dissolution of the powder can require shaking.

The disadvantages connected with the manufacturing and the reconstitution of a lyophilized preparation would be highly reduced if a ready-to-use (RTU) solution of oxaliplatin, whose preparation and administration does not require either lyophilization or reconstitution, were available.

In order to meet the need for solution formulations of oxaliplatin in a RTU form, able to overcome the above-described disadvantages, some formulations have been already proposed, e.g., the Debiopharm and Sanofi-Synthelabo RTU formulations disclosed in the U.S. Pat. Nos. 5,716,988 and 6,306,902, respectively. Both these formulations are reported to be stable RTU formulations containing oxalipatin.

Oxaliplatin formulations with enhanced stability and dosage forms that can be suitably kept for a prolonged period are needed in the art.

The present invention meets these objectives by providing oxaliplatin formulations in a RTU form, with superior stability properties versus the above-identified known RTU preparations. It has now surprisingly been found that the introduction of lactic acid and/or a pharmaceutically acceptable salt thereof as a stabilizing agent in an aqueous solution of oxaliplatin, serves as a novel method of making a formulation with an improved stability versus both the RTU aqueous formulation disclosed in the Debiopharm U.S. Pat. No. 5,716,988 and the aqueous solution stabilized with oxalic acid or an alkali metal salt thereof, disclosed in the Sanofi-Synthelabo U.S. Pat. No. 6,306,902.

DETAILED DESCRIPTION OF THE INVENTION

It is an embodiment of the present invention to provide a stable oxaliplatin solution formulation comprising oxaliplatin, an effective stabilizing amount of lactic acid and/or a pharmaceutically acceptable salt thereof and a pharmaceutically acceptable carrier.

The novel oxaliplatin formulations according to the invention have substantially improved storage stability when compared with the closest known formulations.

No prior art of which applicants are aware describes oxaliplatin formulations as now provided herein.

To the best of applicants' knowledge, the oxaliplatin pharmaceutical formulations of the invention are previously unknown and are not suggested by the art.

A pharmaceutically acceptable salt of lactic acid is, e.g., an alkali metal salt thereof such as, e.g. sodium or potassium, especially sodium lactate.

In a preferred embodiment, the present invention provides a stable oxaliplatin solution formulation comprising oxaliplatin, an effective stabilizing amount of lactic acid and a pharmaceutically acceptable carrier.

In a more preferred embodiment, the invention provides a stable oxaliplatin solution formulation comprising oxaliplatin, an effective stabilizing amount of lactic acid and water as a carrier.

In another aspect, the invention relates to a stable oxaliplatin solution formulation comprising oxaliplatin, an effective stabilizing amount of a pharmaceutically acceptable salt of lactic acid, and a pharmaceutically acceptable carrier.

In a preferred aspect, the invention relates to a stable oxaliplatin solution formulation comprising oxaliplatin, an effective stabilizing amount of an alkali metal salt of lactic acid, and a pharmaceutically acceptable carrier.

In a more preferred aspect, the invention relates to a stable oxaliplatin solution formulation comprising oxaliplatin, an effective stabilizing amount of sodium lactate and a pharmaceutically acceptable carrier.

More particularly, the invention relates to a stable oxaliplatin solution formulation comprising oxaliplatin, an effective stabilizing amount of sodium lactate and water as a carrier.

In a further aspect the invention relates to a stable oxaliplatin solution formulation comprising oxaliplatin, an effective stabilizing amount of lactic acid and a pharmaceutically acceptable salt thereof, and a pharmaceutically acceptable carrier.

A method for stabilizing a formulation of oxaliplatin, which comprises adding an effective stabilising amount of lactic acid and/or a pharmaceutically acceptable salt thereof to an aqueous carrier and then dissolving oxaliplatin in said carrier, is also within the scope of the present invention.

A pharmaceutically acceptable carrier according to the invention can be water or any solution containing water and additional solvents that are soluble/miscible in water, such as for example ethanol, glycerin, propylene glycol and polyoxyethylenglycols, and additional excipients that provide isotonicity to the formulation, such as for example dextrose or saline. Preferably, the carrier is water.

The amount of oxaliplatin present in a formulation according to the invention can range from about 0.1 mg/ml to about 10 mg/ml, preferably from about 2 mg/ml to about 5 mg/ml.

The stabilizing amount of the lactic acid and/or a pharmaceutically acceptable salt thereof can range from a molar concentration of about $5 \cdot 10^{-7}$ M to about 1 M, preferably it can range from about $5 \cdot 10^{-5}$ M to about $5 \cdot 10^{-3}$ M.

The pH of the oxaliplatin solution formulations can range from about 3 to about 9, preferably from about 3 to about 7.

A formulation according to the invention can be prepared by a process comprising the steps of preparing an aqueous carrier with the appropriate amount of the lactic acid and/or the pharmaceutically acceptable salt, and then dissolving oxaliplatin into said carrier.

Preferably the solution of the invention is provided in a sealed container.

The invention also provides for the use of a formulation according to the invention for the treatment of a cancer.

A method for treating a cancer that comprises administering a formulation according to the invention to a patient in need thereof is also within the scope of the present invention. A patient can be a mammal, such as a human.

The term "treating" as used herein, unless otherwise indicated, means reversing, ameliorating, alleviating, inhibiting the progress of, or preventing the disorder or condition to which such term applies, or one or more symptoms of such disorder or condition. The term "treatment", as used herein, refers to the act of treating, as "treating" is defined immediately above.

In the methods according to the invention, the effective dosage of oxaliplatin to be administered to a patient is ranging from about 10 mg/m$^2$ to about 250 mg/m$^2$, more preferably from about 30 mg/m$^2$ to about 180 mg/m$^2$ and most preferably is about 85 mg/m$^2$. However, it will be understood that the therapeutic dosage administered will be determined by the physician in the light of the relevant circumstances including the severity of the condition to be treated and the chosen route of administration. Therefore, the above dosage ranges are not intended to limit the scope of the invention in any way.

Compositions of the invention can be used to treat cancer including, but not limited to: chronic and acute granulocytic leukemia, chronic and acute lymphocytic leukemia, primary marcoglobulinemia, non-Hodgkins' lymphoma, Hodgkin's disease, multipe myeloma, neuroblastom, breast cancer, ovarian cancer, lung cancer, Wilm's tumor, rhabdomyosarcoma, primary thrombocuosis, soft tissue sarcoma, acute lymphocytic leukemia, choriocarcinoma, mycosis fungiodes breast cancer, head and neck cancer, osteogenic sarcoma, testicular cancer, Kaposi's sarcoma, stomach cancer, cervical cancer, colon cancer, bladder cancer, pancreatic cancer, skin cancer, esophageal cancer and genitourinary tract cancer.

It is also an aspect of this invention that a formulation described herein can be combined with other chemotherapeutic agents for the treatment of the diseases and disorders discussed above. For instance, a formulation according to the invention can be combined with alkylating agents such as fluorouracil (5-FU) alone or in further combination with leucovorin; or other alkylating agents such as, without limitation, other pyrimidine analogs such as UFT, capecitabine, gemcitabine and cytarabine; the alkyl sulfonates, e.g., busulfan (used in the treatment of chronic granulocytic leukemia), improsulfan and piposulfan; aziridines, e.g., benzodepa, carboquone, meturedepa and uredepa; ethyleneimines and methylmelamines, e.g., altretamine, triethylenemelamine, triethylenephosphoramide, triethylenethiophosphoramide and trimethylolmelamine; and the nitrogen mustards, e.g., chlorambucil (used in the treatment of chronic lymphocytic leukemia, primary macroglobulinemia and non-Hodgkin's lymphoma), cyclophosphamide (used in the treatment of Hodgkin's disease, multiple myeloma, neuroblastoma, breast cancer, ovarian cancer, lung cancer, Wilm's tumor and rhabdomyosarcoma), estramustine, ifosfamide, novembrichin, prednimustine and uracil mustard (used in the treatment of primary thrombocytosis, non-Hodgkin's lymphoma, Hodgkin's disease and ovarian cancer); and triazines, e.g., dacarbazine (used in the treatment of soft tissue sarcoma). Likewise the formulation of the invention can be expected to have a beneficial effect in combination with other antimetabolite chemotherapeutic agents such as, without limitation, folic acid analogs, e.g. methotrexate (used in the treatment of acute lymphocytic leukemia, choriocarcinoma, mycosis fungiodes breast cancer, head and neck cancer and osteogenic sarcoma) and pteropterin; and the purine analogs such as mercaptopurine and thioguanine which find use in the treatment of acute granulocytic, acute lymphocytic and chronic granulocytic leukemias. The formulation according to the present invention can also be efficacious in combination with natural product based chemotherapeutic agents such as, without limitation, the vinca alkaloids, e.g., vinblastin (used in the treatment of breast and testicular cancer), vincristine and vindesine; the epipodophylotoxins, e.g., etoposide and teniposide, both of which are useful in the treatment of testicular cancer and Kaposi's sarcoma; the antibiotic chemotherapeutic agents, e.g., daunorubicin, doxorubicin, epirubicin, idarubicin, and mitomycin (used to treat stomach, cervix, colon, breast, bladder and pancreatic cancer), dactinomycin, temozolomide, plicamycin, bleomycin (used in the treatment of skin, esophagus and genitourinary tract cancer); nemorubicin and the enzymatic chemotherapeutic agents such as L-asparaginase. In addition to the above, the formulation of the present invention can have a beneficial effect used in combination with other platinum coordination complexes, e.g., cisplatin and carboplatin; substituted ureas such as hydroxyurea; methylhydrazine derivatives, e.g., procarbazine; adrenocortical suppressants, e.g., mitotane, aminoglutethimide; and hormone and hormone antagonists such as the adrenocorticosteriods (e.g., prednisone), progestins (e.g., hydroxyprogesterone caproate); estrogens (e.g., diethylstilbesterol); antiestrogens such as tamoxifen; androgens, e.g., testosterone propionate; and aromatase inhibitors (such as, e.g., formestane, fadrozole, letrozole, anastrozole and exemestane).

A formulation according to the invention can also be active in combination with a topoisomerase I inhibitor such as, e.g., irinotecan (CPT-11), topotecan, rubitecan and lurtotecan.

A number of clinical studies combining the use of oxaliplatin and irinotecan hydrochloride (i.e. CPT-11 CAMPTOSAR®) administered in separated pharmaceutical formulations have been performed with promising efficacy perspectives (ASCO 2002 Abstract numbers 426, 511, 631, 543, 2254 and 529).

A desirable embodiment is therefore to prepare fixed formulations comprising the two active ingredients mixed together in order to improve not only patients' compliance and simplify the administration procedures at the clinical site, but also to reduce the risks of external contamination with cytotoxic drugs due to the inappropriate handling of the formulations to be administered.

Oxaliplatin is well known from the scientific literature for its instability in the presence of acidic media, especially chloride media (Curis et al., Journal Synchrotron Rad (2001) 8, 716–718).

Irinotecan molecule consists of a pentacyclic structure having a lactone in the ring E, which is essential for cytotoxicity. Since the lactone-active form predominates at acidic value of pH, irinotecan is usually salified by means of hydrochloric acid and is formulated in a pH 3.5 solution in order to maintain the lactone form closed.

From the foregoing, it can be concluded that the two active drug substances are incompatible for a co-administration and for a development of a ready-to-use dosage form.

It has now unexpectedly found that the presence of lactic acid or a pharmaceutically acceptable salt thereof as stabilizing agent allows for the preparation of stable ready-to-use formulations comprising the two active ingredients combined in fixed ratios.

It is therefore an embodiment of the present invention a combined pharmaceutical formulation comprising oxaliplatin and irinotecan hydrochloride as active ingredients in fixed ratios, an effective stabilizing amount of lactic acid or a pharmaceutically acceptable salt thereof and a pharmaceutically acceptable carrier.

Advantageously, these combined pharmaceutical formulations do not require any manipulation to the dosage form prior to use, thereby minimizing dosing preparation time and reducing possible sources of contamination.

A weight ratio of oxaliplatin to irinotecan hydrochloride can be in the range from about 2:1 to about 1:1 and from about 1:1 to about 1:20, preferably from about 1:1 to about 1:10, particularly from about 1:1 to about 1:5, for example about 1:1, about 1:2 or about 1:3.

The amount of oxaliplatin present in a combined pharmaceutical formulation according to the invention can range from about 0.1 mg/ml to about 10 mg/ml, preferably from about 2 mg/ml to about 8 mg/ml.

The amount of irinotecan hydrochloride present in a combined pharmaceutical formulation according to the invention can range from about 1 mg/ml to about 30 mg/ml, preferably from about 4 mg/ml to about 24 mg/ml.

The stabilizing amount of lactic acid or a pharmaceutically acceptable salt thereof present in a combined pharmaceutical formulation according to the invention can range from a molar concentration of about $1.10^{-5}$ M to about 1 M, preferably from about $1.10^{-4}$ M to about 0.1M.

A pharmaceutically acceptable carrier has been already defined above and, water is "preferred" carrier in a combined pharmaceutical formulation according to the present invention.

The pH of a combined pharmaceutical formulation according to the invention can range from about 2.5 to about 5, preferably from about 3.0 to about 4.0.

Another embodiment of the present invention is a combined pharmaceutical formulation comprising oxaliplatin and irinotecan hydrochloride as active ingredients in fixed ratios, an effective stabilizing amount of lactic acid or a pharmaceutically acceptable salt thereof and a pharmaceutically acceptable carrier, wherein the weight ratio of oxaliplatin to irinotecan hydrochloride can be in the range from about 2:1 to about 1:1.

A still another embodiment of the present invention is a combined pharmaceutical formulation comprising oxaliplatin and irinotecan hydrochloride as active ingredients in fixed ratios, an effective stabilizing amount of lactic acid or a pharmaceutically acceptable salt thereof and a pharmaceutically acceptable carrier, wherein the weight ratio of oxaliplatin to irihotecan hydrochloride can be in the range from about 1:1 to about 1:20.

A further embodiment of the present invention is a combined pharmaceutical formulation comprising oxaliplatin and irinotecan hydrochloride as active ingredients in fixed ratios, an effective stabilizing amount of lactic acid or a pharmaceutically acceptable salt thereof and a pharmaceutically acceptable carrier, wherein the weight ratio of oxaliplatin to irinotecan hydrochloride can be in the range from about 1:1 to about 1:10.

Optionally the combined pharmaceutical formulations according to the invention can comprise an isotonic agent.

As used herein the term "isotonic agent" means a solute suitable to make a solution isotonic, such as for example, dextrose, sucrose, mannitol, glycerin sorbitol or glycine. According to the present invention, a preferred isotonic agent is sorbitol.

A formulation according to the invention can be prepared by a process comprising the steps of preparing an aqueous carrier with the appropriate amount of lactic acid and/or a pharmaceutically acceptable salt of lactic acid, then controlling and adjusting the pH below about 5, heating the solution at a temperature ranging from about 30 to about 85° C., dissolving irinotecan (e.g. CPT-11) and then adding oxaliplatin into said mixture. The isotonic agent can optionally be added to the said solution.

Preferably the solution of the invention is provided in a sealed container.

A method for stabilizing a combined pharmaceutical formulation according to the invention, which comprises adding an effective stabilizing amount of lactic acid and/or a pharmaceutically acceptable salt thereof to an aqueous carrier maintaining the pH of the solution below about 5, dissolving irinotecan (e.g. CPT-11) and then adding oxaliplatin to said carrier, is also within the scope of the present invention.

It is a still further embodiment of this invention to provide for the use of a combined pharmaceutical formulation according to the invention for treatment of a cancer.

A method for treating a cancer which comprises administering a combined pharmaceutical formulation according to the invention to a patient in need thereof is also within the scope of the present invention.

The following examples illustrate but do not limit in any way the invention. All cited references and patent documents are incorporated by reference herein in their entirety.

EXAMPLES

Example 1

Preparation of Oxaliplatin Solutions

Solutions have been prepared by the following procedure:

Prepare the aqueous carrier by weighing an appropriate amount of organic acid or one of its related salts in order to reach the established molarity; add water for injection to make up to the final volume.

Weigh Oxaliplatin into a suitable container and add the appropriate volume of the aqueous carrier in order to reach, for example 2 mg/ml as final concentration.

Dissolution of the active in the aqueous carrier easily occurs by a simple magnetic stirring or sonication.

The following formulations, as in Table 1, have been prepared.

TABLE 1

| | Non active ingredient (s) | oxaliplatin concentration | pH |
|---|---|---|---|
| FORMULATION 1 | Water for inj. | 2 mg/ml | 6.7 |
| FORMULATION 2 | Sodium oxalate 0.0005 M | 2 mg/ml | 7.1 |
| FORMULATION 3 | Lactic acid 0.0004 M | 2 mg/ml | 3.7 |
| FORMULATION 4 | Acetate 0.1 M | 2 mg/ml | 4.8 |
| FORMULATION 5 | Citrate 0.1 M | 2 mg/ml | 5.1 |

FORMULATION 1 is a representative example of the formulations described in Debiopharm's U.S. Pat. No. 5,716,988.

FORMULATION 2 is a representative example of the formulations described in Sanofi-Synthelabol's U.S. Pat. No. 6,306,902.

FORMULATION 3 is a representative example of a formulation according to the invention.

FORMULATION 4 and FORMULATION 5 are reference formulations described in Sanofi-Synthelabo's U.S. Pat. No. 6,306,902.

Example 2

Stability Study

The above-mentioned formulations in Example 1 have been investigated by an accelerated stability study and the chemical assay of the active has been tested by high performance liquid chromatography (HPLC) after 1 and 3 months of storage at 40° C. and 75% of relative humidity.

Results, expressed as percentage of the weighted amount of the active, are here summarized in the following Table 2.

TABLE 2

|  | 1 month | 3 months |
| --- | --- | --- |
| FORMULATION 1 | 97.1 | 61.9 |
| FORMULATION 2 | 97.5 | 95.4 |
| FORMULATION 3 | 100.0 | 99.5 |
| FORMULATION 4 | 100.5 | 69.2 |
| FORMULATION 5 | 28.5 | Not determined |

The above-tabulated data clearly demonstrate that:

a simple oxaliplatin water solution is not stable after 3 months storage at the the tested conditions;

lactic acid formulation showed a stabilizing capacity on the active more effective than all the other mono and bi-organic acid tested.

Example 3

Stability Study

A second chemical stability study was performed on the following formulations mentioned in Table 3 and prepared by the procedure illustrated in Example 1.

The aim of this second study is to evaluate the stabilizing effect of different concentrations of lactic acid and sodium lactate and different pHs on the active compound.

TABLE 3

|  | Non active ingredients |  | oxaliplatin concentration | pH |
| --- | --- | --- | --- | --- |
| FORMULATION 6 | Lactic Acid | 0.005 M | 2 mg/ml | 3.1 |
| FORMULATION 7 | Lactic Acid | 0.0005 M | 2 mg/ml | 3.8 |
| FORMULATION 8 | Lactic Acid | 0.0001 M | 2 mg/ml | 4.7 |
| FORMULATION 9 | Lactic Acid | 0.00005 M | 2 mg/ml | 5.1 |
| FORMULATION 10 | Sodium Lactate | 0.005 M | 2 mg/ml | 6.3 |

The obtained results are summarized in Table 4 and show how even very low amounts of lactic acid and sodium lactate have a stabilizing capacity on the oxaliplatin water solution.

TABLE 4

|  | 1 month | 2 months |
| --- | --- | --- |
| FORMULATION 6 | 99.5 | 99.0 |
| FORMULATION 7 | 101.4 | 99.5 |
| FORMULATION 8 | 99.5 | 99.5 |
| FORMULATION 9 | 103.0 | 106.0 |
| FORMULATION 10 | 98.0 | 100.5 |

Example 4

Fixed Formulation Combining Oxaliplatin and CPT-11 (Formulation 11)

Said formulation 11 comprises oxaliplatin and CPT-11 as active ingredients in a fixed ratio 1:2 respectively. More preferably, said formulation comprises oxaliplatin in a concentration between about 2 to about 6 mg/ml, CPT-11 in a concentration between about 4 to about 12 mg/ml, dissolved in an aqueous carrier comprising lactic acid in a range between about 0.005M to about 0.009M, to reach a pH of about 3.5.

An adequate amount of sorbitol, in order to produce an isotonic solution, can also be present (Formulation 11).

Example 5

Fixed Formulation Combining Oxaliplatin and CPT-11 (Formulation 12)

Formulation 12 comprises oxaliplatin and CPT-11 as active ingredients in a fixed ratio of 1:3, respectively.

More preferably, the formulation comprises oxaliplatin in a concentration between about 2 to about 8 mg/ml, CPT-11 in a concentration between about 6 to about 24 mg/ml, dissolved in an aqueous carrier comprising lactic acid in a range between about 0.005M to about 0.01M, to reach a pH of about 3.5.

An adequate amount of sorbitol, in order to an isotonic solution, can also be present (Formulation 12).

Example 6

Preparation of a Fixed Formulation Combining Oxaliplatin and CPT-11

The fixed formulation solutions described in examples 4 and 5, can be prepared by the following procedure:

Prepare the aqueous carrier weighing an appropriate amount of lactic acid USP or its pharmaceutically acceptable salt thereof in order to reach the established molarity and pH in a range between about 3.4–3.6; add water for injection. Heat the solution to reach the established temperature in a range from about 30 to about 85° C.

Weigh CPT-11 into a suitable container and add an appropriate volume of the lactic acid solution in order to dissolve the drug; mix by a simple magnetic stirrer approximately for 30 minutes.

At this or another point an isotonic agent can be added to the mixture.

Cool the solution to approximately room temperature; weigh oxaliplatin and add it to the already prepared CPT-11 solution; stir the mixture until a clear solution occurs.

Finally, rinse the container as needed with water for injection to reach, as an example, 5 mg/ml and 10 mg/ml as final concentrations of respectively oxaliplatin and CPT-11.

What is claimed is:

1. A combined pharmaceutical formulation comprising oxaliplatin and irinotecan hydrochloride as active ingredients in fixed weight ratios, an effective stabilizing amount of lactic acid or a pharmaceutically acceptable salt thereof and a pharmaceutically acceptable carrier.

2. A combined pharmaceutical formulation as claimed in claim 1, wherein the fixed weight ratio of oxaliplatin to irinotecan hydrochloride is in the range from about 2:1 to about 1:1.

3. A combined pharmaceutical formulation as claimed in claim 1, wherein the fixed weight ratio of oxaliplatin to irinotecan hydrochloride is in the range from about 1:1 to about 1:20.

4. A combined pharmaceutical formulation as claimed in claim 3, wherein the fixed weight ratio of oxaliplatin to irinotecan hydrochloride is in the range from about 1:1 to about 1:10.

5. A combined pharmaceutical formulation as claimed in claim 1, which further comprises an isotonic agent.

6. A combined pharmaceutical formulation as claimed in claim 5, wherein the isotonic agent is sorbitol.

7. A combined pharmaceutical formulation as claimed in claim 1, wherein the pH of the formulation ranges from about 2.5 to about 5.

8. A combined pharmaceutical formulation as claimed in claim 5, wherein the pH of the formulation ranges from about 2.5 to about 5.

9. A combined pharmaceutical formulation as claimed in claim 1, wherein the oxaliplatin is cis-oxalato(trans-l-1,2-diaminocyclohexane)platinum(II).

10. A combined pharmaceutical formulation as claimed in claim 1, wherein the oxaliplatin is cis-oxalato(trans-l-1,2-diaminocyclohexane)platinum(II) having high optical purity.

11. A combined pharmaceutical formulation as claimed in claim 10, wherein the cis-oxalato(trans-l-1,2-diaminocyclohexane)platinum(II) has a melting point between about 198° C. and about 292° C.

12. A combined pharmaceutical formulation as claimed in claim 10, wherein the cis-oxalato(trans-l-1,2-diaminocyclohexane)platinum(II) has optical purity about equal to or higher than 99.94%.

13. A combined pharmaceutical formulation formulation as claimed in claim 11, wherein the cis-oxalato (trans-1-1, 2-diaminocyclohexane) platinum (II) has a melting point between about 198.3° C. and about 199.7° C.

14. A method for treating preventing, or ameliorating a cancer, which comprises administering a combined pharmaceutical formulation as claimed in claim 1 to a patient in need thereof.

* * * * *